United States Patent
Hilgers et al.

(10) Patent No.: US 11,623,069 B2
(45) Date of Patent: *Apr. 11, 2023

(54) DEVICE WITH MULTIPLE ELECTROACTIVE MATERIAL ACTUATOR UNITS AND ACTUATING METHOD

(71) Applicant: KONINKLIJKE PHILIPS N.V., Eindhoven (NL)

(72) Inventors: Achim Hilgers, Alsdorf (DE); Mark Thomas Johnson, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 540 days.

This patent is subject to a terminal disclaimer.

(21) Appl. No.: 16/611,271

(22) PCT Filed: Jun. 22, 2018

(86) PCT No.: PCT/EP2018/066831
§ 371 (c)(1),
(2) Date: Nov. 6, 2019

(87) PCT Pub. No.: WO2018/234572
PCT Pub. Date: Dec. 27, 2018

(65) Prior Publication Data
US 2020/0164179 A1    May 28, 2020

(30) Foreign Application Priority Data

Jun. 23, 2017 (EP) .................................. 17177661

(51) Int. Cl.
*H01L 21/00* (2006.01)
*G01P 15/08* (2006.01)
(Continued)

(52) U.S. Cl.
CPC .... *A61M 25/0158* (2013.01); *A61M 25/0155* (2013.01); *H01L 41/0825* (2013.01);
(Continued)

(58) Field of Classification Search
CPC ... H01L 41/042; H01L 41/09; A61M 25/0158
(Continued)

(56) References Cited

U.S. PATENT DOCUMENTS 4,815,472 A   3/1989  Wise et al.
5,405,337 A   4/1995  Maynard
(Continued)

FOREIGN PATENT DOCUMENTS

DE    19936961 A1   2/2001
EP     2402830 A1   1/2012
WO  2018134421 A1   7/2018

OTHER PUBLICATIONS

C. Bronnimann "Technische Grundlagen Zur Lonworks Technologie" Mar. 24, 2010 p. 1-31 Retrieved From Internet Jul. 18, 2016.
(Continued)

*Primary Examiner* — Calvin Lee
(74) *Attorney, Agent, or Firm* — Schott, P.C.

(57) ABSTRACT

The proposed device comprises a plurality of electroactive material actuator units arranged as a set. Control data for driving individual units is transferred over three shared
(Continued)

power lines. The electroactive material actuator of each unit is driven depending on control data received from the power lines via a demodulator, a controller, and a driver.

20 Claims, 2 Drawing Sheets

(51) Int. Cl.
*A61M 25/01* (2006.01)
*H01L 41/08* (2006.01)
*H01L 41/09* (2006.01)
*H04B 3/54* (2006.01)
*A61M 25/00* (2006.01)
*A61M 25/09* (2006.01)
*F03G 7/00* (2006.01)

(52) U.S. Cl.
CPC ............. *H01L 41/09* (2013.01); *H04B 3/542* (2013.01); *A61M 2025/0058* (2013.01); *A61M 2025/09133* (2013.01); *F03G 7/004* (2021.08)

(58) Field of Classification Search
USPC ................ 438/50–53; 257/254, 417–419
See application file for complete search history.

(56) References Cited

U.S. PATENT DOCUMENTS

| 5,430,341 | A | 7/1995 | Summer |
| 6,326,936 | B1 * | 12/2001 | Inganas ............... H01L 23/5328 345/55 |
| 8,552,846 | B2 | 10/2013 | Cordoba Matilla |
| 9,257,917 | B1 | 2/2016 | Filardo et al. |
| 10,892,690 | B2 * | 1/2021 | Van Den Ende ..... H01L 41/042 |
| 11,139,425 | B2 * | 10/2021 | Johnson ................ H01L 41/042 |
| 11,251,357 | B2 * | 2/2022 | Johnson ................ H01L 41/193 |
| 11,322,675 | B2 * | 5/2022 | Hilgers ................... F03G 7/005 |
| 11,322,677 | B2 * | 5/2022 | Van De Molengraaf .................... H01L 41/193 |
| 2009/0007758 | A1 | 1/2009 | Scholsser et al. |
| 2016/0301330 | A1 | 10/2016 | Van Kessel |
| 2018/0296186 | A1 | 10/2018 | Harks et al. |

OTHER PUBLICATIONS

International Search Report and Written Opinion from PCT/EP2018/066831 dated Oct. 4, 2018.

* cited by examiner

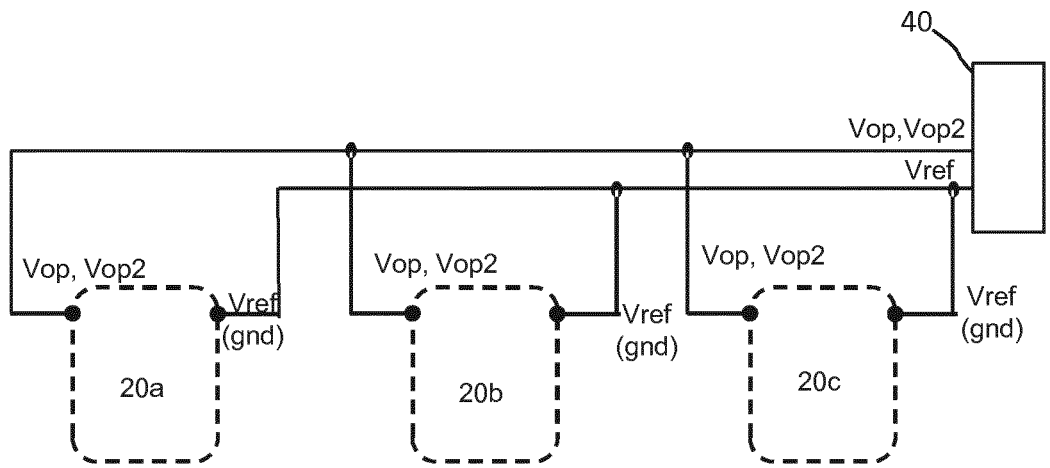
FIG. 4
| I(n) | | | | | | | | D(n) | | | | | | | |
|---|---|---|---|---|---|---|---|---|---|---|---|---|---|---|---|
| 0 | 1 | 2 | 3 | 4 | 5 | 6 | 7 | 0 | 1 | 2 | 3 | 4 | 5 | 6 | 7 |
FIG. 5
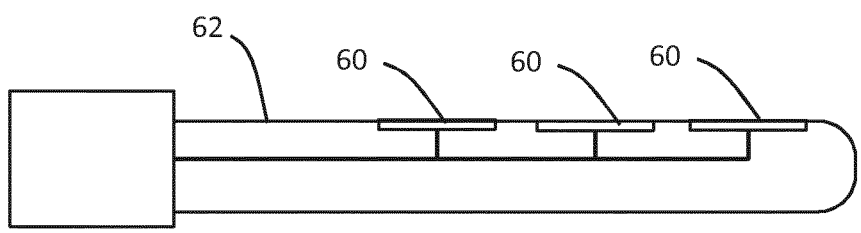
FIG. 6

DEVICE WITH MULTIPLE ELECTROACTIVE MATERIAL ACTUATOR UNITS AND ACTUATING METHOD

CROSS-REFERENCE TO PRIOR APPLICATIONS

This application is a continuation of U.S. application Ser. No. 16/478,248, filed on Jul. 16, 2019, now U.S. Pat. No. 11,322,675 issued May 3, 2022, which is the U.S. National Phase application under 35 U.S.C. § 371 of International Application No. PCT/EP2018/066831, filed on Jun. 22, 2018, which claims the benefit of EP Patent Application No. EP 17177661.0, filed on Jun. 23, 2017. These applications are hereby incorporated by reference herein.

This invention relates to actuator devices which make use of electroactive materials, such as electroactive polymers.

BACKGROUND OF THE INVENTION

Electroactive polymers (EAP) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP material give rise to applicability to new applications.

An EAP device can be used in any application in which a small amount of movement of a component or feature is desired, based on electric actuation. Similarly, the technology can be used for sensing small movements.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-20 kHz.

Devices using electroactive polymers can be subdivided into field-driven and ionic-driven materials.

Examples of field-driven EAPs are dielectric elastomers, electrostrictive polymers (such as PVDF based relaxor polymers or polyurethanes) and liquid crystal elastomers (LCE).

Examples of ionic-driven EAPs are conjugated polymers, carbon nanotube (CNT) polymer composites and Ionic Polymer Metal Composites (IPMC).

Field-driven EAPs are actuated by an electric field through direct electromechanical coupling, while the actuation mechanism for ionic EAPs involves the diffusion of ions. Both classes have multiple family members, each having their own advantages and disadvantages.

FIGS. 1 and 2 show two possible operating modes for an EAP device.

The device comprises an electroactive polymer layer 14 sandwiched between electrodes 10, 12 on opposite sides of the electroactive polymer layer 14.

FIG. 1 shows a device which is not clamped. A voltage is used to cause the electroactive polymer layer to expand in all directions as shown.

FIG. 2 shows a device which is designed so that the expansion arises only in one direction. The device is supported by a carrier layer 16. A voltage is used to cause the electroactive polymer layer to curve or bow.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the electroactive polymer, or it may result from asymmetry in the properties of the carrier layer, or a combination of both.

Due to their inherent small form factor, electroactive polymers are well suited to be used in applications were multiple functions need to be realized, and thus where multiple actuators are need. For example, in certain applications, an array of actuators can be useful, for instance in positioning systems and controlled topology surfaces.

However, a basic interconnection solution would require at least one wire or cable to be connected to each of the actuators and additionally one (common) ground connection. The higher the number of actuators, the more complex the electrical connections become. If hundreds of actuators need to be addressed for example in a matrix like approach, this cannot easily be realized by a conventional wiring scheme, especially if small form factors such as in mobile devices or medical surgery equipment, are required.

For example, in a catheter or guide wire based device, it would be impractical to have all actuator devices individually controlled by wires emerging from the end of the device, as this would require the wires to run throughout the length of the device. In practical situations there is no space to accommodate these wires, and in addition the wires would reduce the maneuverability of the device.

Long wires are also prone to defects (breakage or short circuits) which would especially be the case if the wires were made thin.

An alternative approach which enables a reduction in connection lines is to use a matrix addressing scheme.

A passive matrix array is a simple implementation of an array driving system using only row (n rows) and column (m columns) connections. Only (n+m) drivers are required to address up to (n×m) actuators. This provides a cost effective approach which also reduces the am amount of wiring.

However, a passive matrix EAP actuator array will suffer from cross talk between adjacent actuators. When voltage is applied to actuate one actuator, the actuators around it also experience a voltage and will partially actuate, which is an unwanted effect for many applications. This means there is a best actuation contrast ratio which can be achieved. Hence, with a passive matrix addressing scheme it is not straightforward to individually address each actuator independently of the others.

The use of an active matrix for addressing arrays of electroactive polymer actuators has been contemplated, for example for electronic braille applications. An active matrix approach involves providing a switching device at each electroactive polymer actuator, at the intersection of a row conductor and a column conductor. In this way, each actuator in the array can, if desired, be individually actuated.

However, this requires a cyclic addressing sequence, so that the array of devices is not truly addressed simultaneously. There is also still a significant number of electrical connections required, for all of the rows and columns of the array.

Another issue is that each actuator and controller arrangement may require both high voltage actuator voltages, typically around 200V, and low voltage control voltages for the control electronics. This again implies additional connections to the actuator.

SUMMARY OF THE INVENTION

There is therefore a need for an addressing scheme which can address a multiplicity of EAPs whilst simultaneously providing the high and the low voltages required for operation of the system and using a reduced number of electrical connections.

It is an object of the current invention to fulfill the aforementioned need at least partially. This object is achieved at least partially by the invention as defined by the independent claims. The dependent claims provide advantageous embodiments.

According to examples in accordance with an aspect of the invention, there is provided a device comprising:
a plurality of electroactive material actuator units arranged as a set, each electroactive material actuator unit comprising three power line terminals; and
three power lines comprising a common reference power line, a controller power line and a driver power line, wherein each electroactive material actuator unit is connected in parallel between the three power lines, the three power lines connecting to the three power line terminals;
wherein each electroactive material actuator unit comprises:
an electroactive material actuator;
a demodulator for demodulating a data signal carried by at least one of the power lines;
a controller for receiving data from the demodulated data signal; and
a driver for driving the electroactive material actuator in dependence on the received data.

The units of the set receive the same power line signals, and hence are connected in parallel across the at least two power lines. The physical configuration may however be in any desired shape.

This device makes use of a data modulation over at least one power line to address multiple actuators. The actuator units are also powered by common power lines (they are in parallel between those power lines) so that a small set of power lines are used to control all actuator units, and there is no need for additional dedicated data lines. The at least one of the power lines is used as a data bus.

This design thus enables a small form factor for the overall device with a small number of electrical connections which need to be routed to and from the actuator units.

The device comprises three power lines, comprising a common reference power line, a controller power line and a driver power line, wherein each electroactive material actuator unit comprises three corresponding power line terminals. As a result, the circuitry at each unit can be simplified, by supplying two different power supplies to the units.

The at least one of the power lines on which the data signal is modulated may be the controller power line. This carries a lower voltage than the driver power line, so that the modulation and demodulation process is made simpler.

One power line may carry first modulated data in the form of actuation level data and another one of the power lines may carry second modulated data in the form of addressing data. In this way, the encoded data is simplified. One power line carries data to identify a particular EAM unit, and the other carries the actuation level to be implemented by that EAM unit.

In another example, one power line carries a power ramp signal and another one of the power lines carries modulated data in the form of addressing and timing data for sampling the power ramp signal for an addressed unit at a particular time. In this way, data demodulation takes place, and then a variable power level is selected for application to the unit identified by the demodulated signal. The unit then preferably has a local storage capacitor to store its drive level between successive drive signals.

The data signal which is modulated onto the at least one power line may comprise a unique address associated with a specific actuator unit and a data signal for that actuator unit. Thus, the actuator units may be individually addressed.

Each electroactive material unit may comprise a sub-set of electroactive material elements, wherein the data signal comprises commands for each electroactive material element of the sub-set. This provides addressing of actuator units which themselves comprises a cluster of actuator elements, for example to provide multidimensional actuation (2D or 3D).

Each electroactive material actuator unit may further comprises a modulator for modulating a data signal onto at least one of the power lines. This means the bus system enables bidirectional communication, either between the actuator unit and a general system controller, or between multiple actuator units.

A device controller is for example used for providing power and data signals on the power lines. The device controller may for example provide a data signal which comprises a set of identification words and data words in series, each identification word associated with a respective one of the electroactive material actuator units, wherein the controller of each electroactive material actuator unit is adapted to recognize its own associated identification word and read the associated data word. Thus, all units receive the same data signal over the shared modulated power line, but different portions are linked to different identities. This means each unit needs to know its own identity so that the relevant data word can be identified within the data signal.

The electroactive material actuators for example comprise electroactive polymer actuators.

The invention also provides a catheter comprising a device as defined above, wherein the plurality of electroactive material actuator units are for steering control of the catheter.

Examples in accordance with another aspect of the invention provide a method of actuating a device which comprises:
a plurality of electroactive material actuator units arranged as a set, each electroactive material actuator unit comprising three power line terminals; and
three power lines comprising a common reference power line, a controller power line and a driver power line, wherein each electroactive material actuator unit is connected in parallel between the three power lines, the three power lines connecting to the three power line terminals,
wherein the method comprises:
providing power signals on the three power lines;
providing a data signal modulated onto at least one of the power lines;
at each individual electroactive material actuator:
demodulating a data signal carried by the at least one of the power lines;

receiving data from the demodulated data signal; and
driving the electroactive material actuator in dependence on the received data.

This method enables a shared power line to be used for providing data communication to all units.

At each electroactive material actuator unit, a first power supply on the controller power lines may be used for a local controller and a second power supply on the driver power line may be used for a local driver.

The method steps may be implemented at least in part by software.

BRIEF DESCRIPTION OF THE DRAWINGS

Examples of the invention will now be described in detail with reference to the accompanying drawings, in which:

FIG. 4 shows a set of units of FIG. 3 connected together to form a device;

FIG. 5 shows a data signal structure for the device of FIG. 3; and

FIG. 6 shows a catheter which makes use of a set of actuators for steering control.

DETAILED DESCRIPTION OF THE EMBODIMENTS

The invention provides a device (and operating method for the device) which comprises a plurality of electroactive material actuator units arranged as a set. Data for controlling the driving of the individual units is modulated over a shared power line. The electroactive material actuator units are controlled in dependence on received data from the data line.

The invention provides a reduced complexity of the wiring when multiple actuators need to be addressed and controlled in small application environments.

A most reduced implementation in terms of the power line arrangement could make use of only a single power supply line and a ground connection. However, the invention makes use of two non-ground power lines (so there are three power lines altogether), so that no power conversion needs to take place in the actuator units. They are supplied with separate drive power and controller power. All actuator units are connected in parallel to the power lines and are controlled by a control signal, which is modulated on top of the power supply line.

Figure 1:
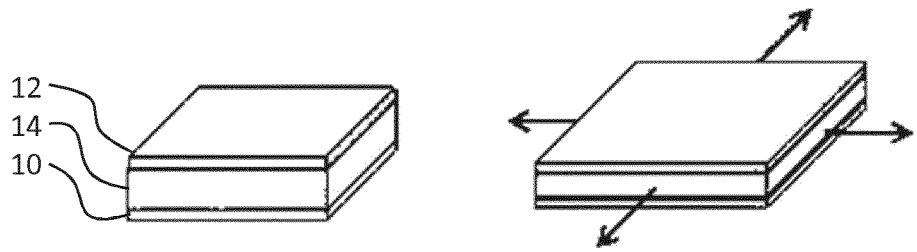
FIG. 1 shows a known electroactive polymer device which is not clamped.
Figure 2:
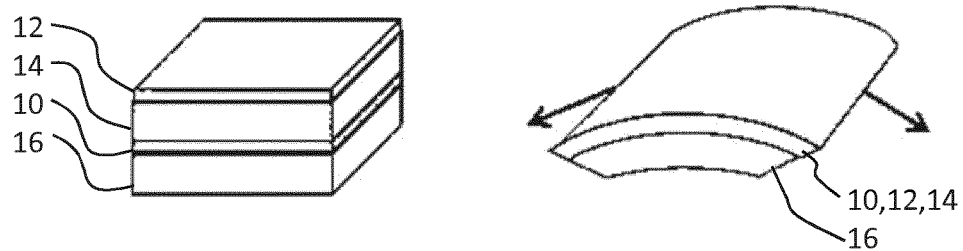
FIG. 2 shows a known electroactive polymer device which is constrained by a backing layer.
Figure 3:
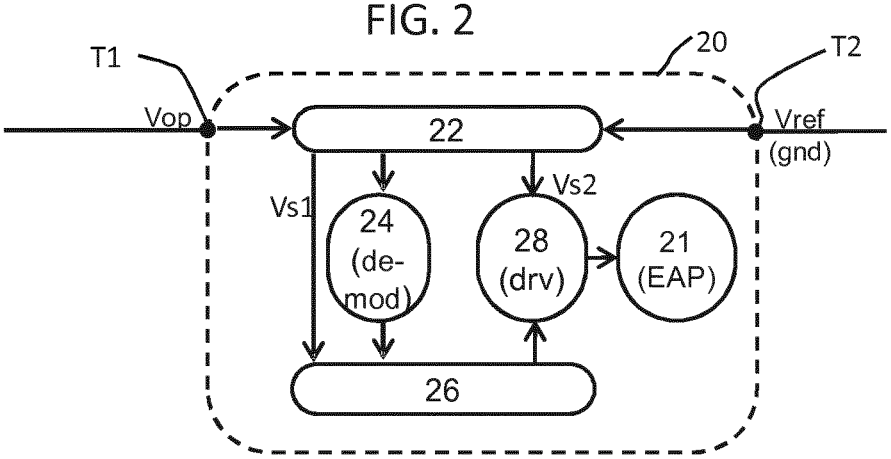
FIG. 3 shows a two examples of an electroactive material actuator unit, one of which is in accordance with the invention.
Figure 3:
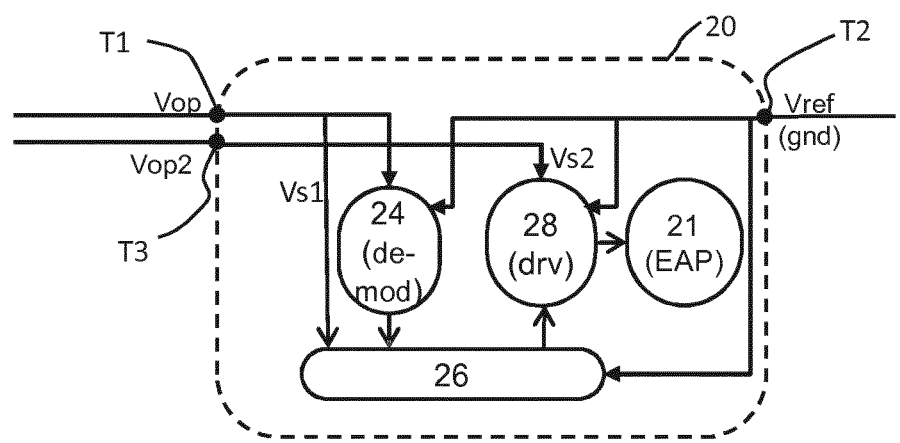

FIG. 3 shows two possible examples of an electroactive material actuator unit 20. Multiple such units are intended to form an overall device, with the units arranged as a set. There may typically be tens or hundreds of actuator units. Each electroactive material actuator unit 20 comprises two power line terminals T1, T2 in the first example (which is not in the scope of this invention) and three power line terminals T1, T2, T3 in the second example, which is in accordance with the invention.

A most simple implementation, in terms of the supply to the actuator units, could use only two power line terminals, and this most simple implementation will first be described. It is shown in the top part of FIG. 3.

The top part of FIG. 3 shows a first power line Vop on which an operating voltage is provided, which connects to a first power line terminal T1 of the unit 20. A reference voltage Vref forms a second power line and connects to a second power line terminal T2, and this may be ground. Data is provided modulated over the power line Vop in the form of a data signal.

The electroactive material actuator unit 20 comprises an electroactive material actuator 21. There may be one or more such actuators within each unit 20. The unit 20 comprises a demodulator 24 for demodulating the data signal. A digital controller 26 receives the demodulated data from the demodulator 24. It interprets driving commands, which are then used to control a driver 28 for driving the electroactive material actuator 21 in dependence on the received data.

To minimize the number of external lines needed, the example of the top part of FIG. 3 has a power unit 22. The power unit comprises a power converter for deriving a first power supply Vs1 for the controller 26 and a second power supply Vs2 for the driver 28 from the signal Vop on the first power line. By providing the power unit 22 in each unit 20, a second power supply Vop2 is not needed.

The power unit 22 may be fed by an AC or preferably a DC voltage. Depending on the voltage amplitude, the power unit needs to be able to convert the input voltage into a (low) DC operation voltage for the digital logic part(s) and/or into a (high) DC voltage suited to operate the actuator. If a high operation voltage (Vop) is used, then the power unit only needs to down-convert the voltage, to generate the low DC operation voltage for the digital control.

The power unit thus may comprise an AC/DC converter. It may comprise a DC to DC voltage up-converter and/or a DC to DC voltage down-converter. Thus, depending on the overall power signal supplied, the voltage may be increased to reach the driver supply, or decreased to reach the digital controller supply, or both (for example if an intermediate voltage is provided). The first power supply (Vop) may for example deliver a medium level voltage amplitude so that a relatively low up-conversion factor is still required to reach the desired voltage Vs2 to supply the driver.

The invention provides an arrangement in which two (non-ground) power supplies are provided (Vop1, Vop2) as well as the reference, thus making three power supplies. This means the units do not need internal power conversion capability shown in the top part of FIG. 3 and described above.

The resulting arrangement is shown in the bottom part of FIG. 3. There is a third power line Vop2 and the actuator unit has an associated third power line terminal T3. The three power lines comprise a common reference power line (Vref) which is provided to the controller, driver and demodulator, a controller power line (Vop) for the controller and demodulator, and a driver power line (Vop2) for the driver.

The use of two non-ground power supplies results in much smaller units since no (or only small) power conversion units are required. The units need two internal power supplies because high voltages are needed to drive the actuator (e.g. 100V or more) whereas a low voltage (e.g. 5V) is needed to power the digital circuitry.

The unit also includes a digital to analogue converter which receives the demodulated (digital) data and derives suitable analog driving signals for the driver. In the example shown, the digital to analog converter may be part of the controller 26. It is used to enable interpretation of the digital commands on the data line, so that the driver can be controlled to deliver a corresponding analog actuation level to the actuator.

Digital to analog converters are available as integrated circuits but also can be made in analogue electronics. A preferred solution is based on using a simple (low cost) microcontroller, for digital to analog conversion as well as for further processing functions.

The units of FIG. 3 are designed for connection in parallel to the two or three power lines, and avoid the need for a dedicated data line.

When only one external power supply (in addition to a reference) is provided, the unit 20 needs only two electrical wires to power and control any number of units, essentially connected via a communications and power bus. When two external power supplies (in addition to a reference) are provided, three electrical wires are used, but the actuator units can be smaller, and have lower power consumption and hence reduced thermal impact. In FIG. 3, any required passive components, such as parallel capacitors at each power supply terminal, are not shown.

FIG. 4 shows three electroactive material actuator units 20a, 20b, 20c connected in parallel between the three power lines Vop, Vop2 and Vref, with the power line signals (one of which may simply be ground) provided by a device controller 40 for providing the power and data signals on the power lines. The two non-ground power lines are shown as a single line for simplicity of the figure.

All of the electronics for each actuator unit may be integrated into one chip (e.g. an application specific integrated chip, ASIC) with, if required, only a few power components connected to it. For example, most of the analogue and digital electronics may be combined and integrated in an ASIC with only limited passive components (e.g. inductors and capacitors) and/or active components (e.g. transistors) connected to it.

Each actuator unit 20a, 20b, 20c needs to react on the reception of a digital signal stream, so that the deflection is controlled based on the digital information.

This may be achieved by providing data in the form of an address identification followed by driving data.

FIG. 5 shows an example of a data signal which comprises a set of identification words and data words in series, each identification word associated with a respective one of the electroactive material actuator units. The controller of each unit then recognizes its own associated identification word and reads the associated data word. In particular, in order to differentiate between the single units, it is not possible to send only data words relating to the status of a unit. In addition to this, the data signal needs to define to which unit the actual digital information belongs.

FIG. 5 shows one identification word I(n) and data word D(n) pair. The data format of FIG. 5 is prepared for each unit and sent together on the bus. With an 8-bit address resolution, up to 256 units may be addressed. If more bits are used, more units could be addressed as well. In such a system, the main controller 40 needs to have all the address information of the whole device configuration. If the original configuration is changed (by adding or taking out units), this needs to be announced in the control software.

All units listen continuously to the data line. As soon as a unit recognizes its own address, the following digital information will be interpreted as actuation information for this specific unit. Digital information can be sent continuously for all units one after each other without any specific order, or also in a specific order, so that high priority units will be addressed first, or so that nearest units will be addressed first.

An alternative approach is that data could be sent only for those units whose status needs to be changed. In such a case, all units may be deactivated or brought into their original position, before ending the application.

The invention may be implemented using known power line communications technology. Such technology is known for sending control information via a common power line to which several network devices are connected in parallel. Power line communication is well known for in-house communication, where network communication links are realized via the mains power line (or lines) in a building. There is an IEEE Power Line Communication Standards Committee setting out standards for such systems.

In general, a network controller (modem/router) is connected to the mains via an adapter. Through the mains wiring, the power as well as modulated digital information is transmitted within the whole network, to all devices connected to the mains. Each device of the power line communication network is connected via its own adapter, which separates the digital information from the mains power. The local adapter performs filtering and modulating (for transmitting) and demodulating (for receiving) functions. Each device within a power line communication network has its own and unique address (e.g. an IP and MAC address).

Instead of the 50 Hz (or 60 Hz) mains frequency also other AC or even Dc signals can be used as the data signal carrier. Thus, a DC power line may also be used.

In one example, the power line Vop carries a high operation voltage (e.g. Vop of about 200 V-300 V), so that in a two-line approach, the power unit only needs to perform down conversion, to generate the low DC operation voltage for the digital control (e.g. 3V). If using low voltage current-driven ionic EAPs (iEAPs), the power conversion module could be very simple, since the digital operation voltage and the EAP operating voltage may be almost equal. Such iEAPs may also be designed to match the operation voltage of the digital (and/or analogue) control parts for example to be in the range of e.g. 3V.

The use of two (or even more) voltage lines in addition to the common ground, as explained above results in much smaller units, since no (or small conversion factor) power conversion units would be required, but this would require an additional power line. In that case, the modulated data signal may be provided on either one of the power supply lines but preferably on the lower voltage line, or indeed there may be data modulated on both power lines (other than ground).

One supply line may be used for address modulation (i.e. to provide device identification) and the other supply line may be used for actuation modulation. Thus, if the address is transmitted on one power line, the other power line may send the corresponding activation information (correlated to the voltage/current amplitude to which the corresponding EAP should be activated).

The modulation and demodulation functions may be implemented in various ways. A basic solution is to implement a simple high-pass filter transferring high frequency control signals from the DC or low frequency supply voltage but blocking all other signals (DC or low mains frequency). This simple demodulation may already be sufficient, if only few EAPs are connected in the application.

However, if more EAPs are connected to the same power line (or to improve the signal to noise ratio), more complicated modulation and demodulation may be used.

The control electronics may be based on a simple low-cost microcontroller for digital to analog conversion, but also for some further processing.

The digital control information can be transmitted via the common power line in many known ways. In a simplest implementation, binary information is directly modulated, e.g. as a rectangular pulse pattern, on a DC carrier signal defined by the DC power bus. The binary information may be coded according to known coding algorithms in order to improve the signal transmission quality. However this still may result in a high exposure to disturbing signals (and in general to any noise). Therefore, a higher frequency AC carrier signal may be superimposed onto a DC power signal, acting as additional AC carrier, on which the digital information is modulated. Again several known modulation schemes can be used.

The EAP actuators may be formed as clusters. For example, one actuator unit may comprise a set of three actuator elements for example to generate a 3D-movement/displacement per actuator unit. This may be realized either by assigning more than one address to such a multi EAP actuator (e.g. one for each EAP element within one unit), or by software coding so that commands are provided for addressing all of the individual elements within the unit.

The communication may be bidirectional so that the units can send and receive data on the power line. For example they can listen to the bus, and if no data is being sent, new data can be provided to the bus creating a time multiplex solution. Other communication principles such as frequency or code multiplex solutions or others may be implemented. This bidirectional communication ability enables a unit to provide feedback of the current actuation (deflection) state or any other sensing information (pressure, force, etc.). The EAP unit may be used as a sensor in addition to an actuator.

For such a two-way communication, data not only needs to be received (demodulated/filtered) in each of the EAP units, but also needs to be modulated and sent via the power line. Thus, in addition to the demodulator unit, a modulator unit also needs to be implemented in each of the EAP units. The main controller of the overall system then also needs to have a demodulator function (in addition to its modulator function) in order to extract information sent from the EAP units and finally to process the data (e.g. for performing calculations or simply displaying). A bidirectional communication between EAP units may also be realized, without involving the main controller/master.

One application of interest is in catheters or guide wires. In this application, there is a very limited space for connection wires and also a requirement that multiple wires do not adversely affect the stiffness.

FIG. 6 shows a set of electroactive material actuators 60 formed along a catheter 62. Each actuator can be actuated to implement a local bending function so that the catheter can be steered. The device may in the same way be provided along or at the tip of a guide wire, such as a catheter guide wire or a stent delivery guide wire. Actuation of the device may be performed generally to induce bending, for example for steering as mentioned above, but also for scanning or motion compensation.

Electroactive material sensors may also be provided for example for measuring flow and/or pressure. For flow pressure sensing, a sag induced in a device depends on the pressure.

The electroactive material actuator preferably comprises an electroactive polymer structure for providing a mechanical actuation. The structure defines a non-actuated state and at least one actuated state (different from the non-actuated state) attainable by application of the electrical drive signal to the electroactive polymer structure. The actuator has an electrode arrangement for providing the drive signal to the EAP material. The electrode structure can be attached to the EAP material directly or with intermediate layers in between.

The EAP material layer of each unit may be sandwiched between electrodes of the electrode structure. Alternatively, electrodes can be on a same side of the EAP material. In either case, electrodes can be physically attached to the EAP material either directly without any (passive) layers in between, or indirectly with additional (passive) layers in between. However, this need not always be the case. For relaxor or permanent piezoelectric or ferroelectric EAPs, direct contact is not necessary. In the latter case, electrodes in the vicinity of the EAPs suffices as long as the electrodes can provide an electric field to the EAPs, the electroactive polymer structure will have its actuation function. The electrodes may be stretchable so that they follow the deformation of the EAP material layer.

The electrical drive signal can be a voltage signal or a current signal depending on the EAP material used (see herein below).

Materials suitable for the EAP layer are known. Electroactive polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class of dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Additional passive layers may be provided for influencing the behavior of the EAP layer in response to an applied electric field.

The EAP layer may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

The materials for the different layers will be selected for example taking account of the elastic moduli (Young's moduli) of the different layers.

Additional layers to those discussed above may be used to adapt the electrical or mechanical behavior of the device, such as additional polymer layers.

The EAP devices may be electric field driven devices or ionic devices. Ionic devices may be based on ionic polymer metal composites (IPMCs) or conjugated polymers. An ionic polymer metal composite (IPMC) is a synthetic composite nanomaterial that displays artificial muscle behavior under an applied voltage or electric field.

IPMCs are composed of an ionic polymer like Nafion or Flemion whose surfaces are chemically plated or physically coated with conductors such as platinum or gold, or carbon based electrodes. Under an applied voltage, ion migration and redistribution due to the imposed voltage across a strip of IPMCs result in a bending deformation. The polymer is a solvent swollen ion exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

The device may be used as a single actuator, or else there may be a line or array of the devices, for example to provide control of a 2D or 3D contour.

The invention can be applied in many EAP applications where an array of actuators is of interest.

In many applications the main function of the product relies on the (local) manipulation of human tissue, or the actuation of tissue contacting interfaces. In such applications EAP actuators provide unique benefits mainly because of the small form factor, the flexibility and the high energy density. Hence EAPs can be easily integrated in soft, 3D shaped and/or miniature products and interfaces. Examples of such applications are:

Skin cosmetic treatments such as skin actuation devices in the form of EAP based skin patches which apply a constant or cyclic stretch to the skin in order to tension the skin or to reduce wrinkles;

Respiratory devices with a patient interface mask which has an EAP based active cushion or seal, to provide an alternating normal pressure to the skin which reduces or prevents facial red marks;

Electric shavers with an adaptive shaving head. The height of the skin contacting surfaces can be adjusted using EAP actuators in order to influence the balance between closeness and irritation;

Oral cleaning devices such as an air floss with a dynamic nozzle actuator to improve the reach of the spray, especially in the spaces between the teeth. Alternatively, toothbrushes may be provided with activated tufts;

Consumer electronics devices or touch panels which provide local haptic feedback via an array of EAP transducers which is integrated in or near the user interface;

Catheters with a steerable tip to enable easy navigation in tortuous blood vessels. The actuator function for example controls the bending radius to implement steering, as explained above.

Another category of relevant application which benefits from EAP actuators relates to the modification of light. Optical elements such as lenses, reflective surfaces, gratings etc. can be made adaptive by shape or position adaptation using EAP actuators. Here the benefits of EAP actuators are for example the lower power consumption.

The data signals used in the system are typically generated by software running on a central controller (to generate the driving data in the form of the combined data signal) and they are read by software running locally at each EAP actuator to extract the relevant data word and process the data signal, if required.

A controller is used to run the software. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A method of actuating a device the device comprising, a plurality of electroactive material actuator units arranged as a set, and three power lines, wherein each electroactive material actuator unit comprises three power line terminals, wherein the three power lines comprise a common reference power line, a controller power line, and a driver power line, wherein the each electroactive material actuator unit is connected in parallel between the three power lines, and wherein each of the three power lines connect to one of the three power line terminals; the method comprising:
   providing power signals on the three power lines;
   providing a data signal, wherein the data signal is modulated onto at least one of the three power lines;
   demodulating a data signal carried by the at least one of the three power lines for the each electroactive material actuator unit;
   receiving data from the demodulated data signal for the each electroactive material actuator unit; and
   driving the each electroactive material actuator unit in dependence of the received data.

2. The method as claimed in claim 1,
   wherein a first power line of the three power lines carries a power ramp signal,
   wherein a second power line of the three power lines carries modulated data in form of addressing and timing data,
   wherein the addressing and timing date are arranged to sample the power ramp signal for an addressed circuit at a particular time, and wherein the second power line is different from the first power line.

3. The method as claimed in claim 1,
wherein a first power line of the three power lines carries first modulated data in form of actuation level data,
wherein a second power line of the three power lines carries second modulated data in form of addressing data, and
wherein the second power line is different from the first power line.

4. The method as claimed in claim 1,
wherein the each electroactive material actuator unit further comprises a modulator circuit, and
wherein the modulator circuit is arranged to modulate a data signal onto at least one of the three power lines.

5. The method as claimed in claim 1,
wherein the each electroactive material unit comprises a sub-set of electroactive material elements, and
wherein the data signal comprises commands for each electroactive material element of the sub-set.

6. The method as claimed in claim 1, further comprising:
supplying power on the controller power line for a local controller circuit using a first power supply, and
supplying power on the driver power line for a local driver circuit using a second power supply.

7. The method as claimed in claim 1, wherein the data signal modulated onto at least one power line comprises a unique address associated with a specific actuator unit and a data signal for the specific actuator unit.

8. The method as claimed in claim 1, further comprising a device controller circuit, wherein the device controller circuit is arranged to provide power signals and data signals on the three power lines.

9. A computer program stored on a non-transitory medium, wherein the computer program when executed on processor performs the method as claimed in claim 1.

10. The method as claimed in claim 1, wherein the at least one of the three power lines on which the data signal is modulated is the controller power line.

11. A device comprising:
a plurality of electroactive material actuator units arranged as a set, wherein each electroactive material actuator unit comprises three power line terminals; and
three power lines,
wherein the three power lines comprise a common reference power line, a controller power line, and a driver power line,
wherein the each electroactive material actuator unit is connected in parallel between the three power lines,
wherein each of the three power lines connect to one of the three power line terminals, and
wherein the each electroactive material actuator unit comprises:
an electroactive material actuator;
a demodulator circuit, wherein the demodulator circuit is arranged to demodulate a data signal carried by at least one of the three power lines;
an actuator controller circuit, wherein the actuator controller circuit is arranged to receive data from the demodulated data signal; and
a driver circuit, wherein the driver circuit is arranged to drive the electroactive material actuator in dependence on the received data.

12. The device as claimed in claim 11,
wherein a first power line of the three power lines carries a power ramp signal,
wherein a second power line of the three power lines carries modulated data in form of addressing and timing data,
wherein the addressing and timing date are arranged to sample the power ramp signal for an addressed circuit at a particular time, and
wherein the second power line is different from the first power line.

13. The device as claimed in claim 11,
wherein a first power line of the three power lines carries first modulated data in form of actuation level data,
wherein a second power line of the three power lines carries second modulated data in form of addressing data, and
wherein the second power line is different from the first power line.

14. The device as claimed in claim 11,
wherein the each electroactive material actuator unit further comprises a modulator circuit, and
wherein the modulator circuit is arranged to modulate a data signal onto at least one of the three power lines.

15. The device as claimed in claim 11,
wherein the each electroactive material unit comprises a sub-set of electroactive material elements, and
wherein the data signal comprises commands for each electroactive material element of the sub-set.

16. The device as claimed in claim 11, wherein the data signal modulated onto at least one power line comprises a unique address associated with a specific actuator unit and a data signal for the specific actuator unit.

17. The device as claimed in claim 11, wherein the at least one of the three power lines on which the data signal is modulated is the controller power line.

18. A catheter comprising a device as claimed in claim 11, wherein the plurality of electroactive material actuator units are arranged to steer the catheter.

19. The device as claimed in claim 11, further comprising a device controller circuit, wherein the device controller circuit is arranged to provide power signals and data signals on the three power lines.

20. The device as claimed in claim 19,
wherein the device controller circuit is arranged to provide an identification data signal,
wherein the identification data signal comprises a set of identification words and data words in series,
wherein each identification word is associated with a respective one of the plurality of electroactive material actuator units, and
wherein each actuator controller circuit is arranged to recognize its own associated identification word and read the associated data word.

* * * * *